United States Patent [19]
Meulink et al.

[11] Patent Number: 5,888,245
[45] Date of Patent: Mar. 30, 1999

[54] ROTATIONAL ALIGNMENT GUIDE FOR A PROSTHETIC HIP STEM IMPLANT AND METHOD OF USING SAME

[75] Inventors: Steven Lee Meulink, Winona Lake; David A. Mann, Warsaw, both of Ind.

[73] Assignee: Bristol-Myers Squibb Company, New York, N.Y.

[21] Appl. No.: 861,434

[22] Filed: May 21, 1997

[51] Int. Cl.[6] ................................. A61F 2/36; A61F 5/00; A61B 17/92
[52] U.S. Cl. .................................. 623/23; 606/86; 606/99
[58] Field of Search .............................. 606/86, 99, 102, 606/87, 89; 623/16, 18, 23

[56] References Cited

U.S. PATENT DOCUMENTS

| | | | |
|---|---|---|---|
| 5,002,578 | 3/1991 | Luman | 623/23 |
| 5,064,427 | 11/1991 | Burkinshaw | 606/99 |
| 5,171,324 | 12/1992 | Campana et al. | 606/99 |
| 5,207,682 | 5/1993 | Cripe | 606/96 |
| 5,342,362 | 8/1994 | Kenyon et al. | 606/79 |
| 5,476,466 | 12/1995 | Barrette et al. | 606/86 |
| 5,514,136 | 5/1996 | Richelsoph | 606/86 |

*Primary Examiner*—David J. Isabella
*Attorney, Agent, or Firm*—Todd A. Dawson

[57] ABSTRACT

The invention is directed to an alignment device for aligning a prosthetic hip stem implant with an opening formed in a proximal femur. The hip stem implant includes a landmark and the proximal femur includes a visual alignment mark. The alignment device includes an implant engaging portion configured for attachment with the landmark on the hip stem implant. The alignment device also includes a needle indicator connected with the implant engaging portion and having an end which may be positioned relative to the visual alignment mark on the proximal femur, thereby aligning the prosthetic hip stem implant relative to the opening in the proximal femur.

9 Claims, 2 Drawing Sheets

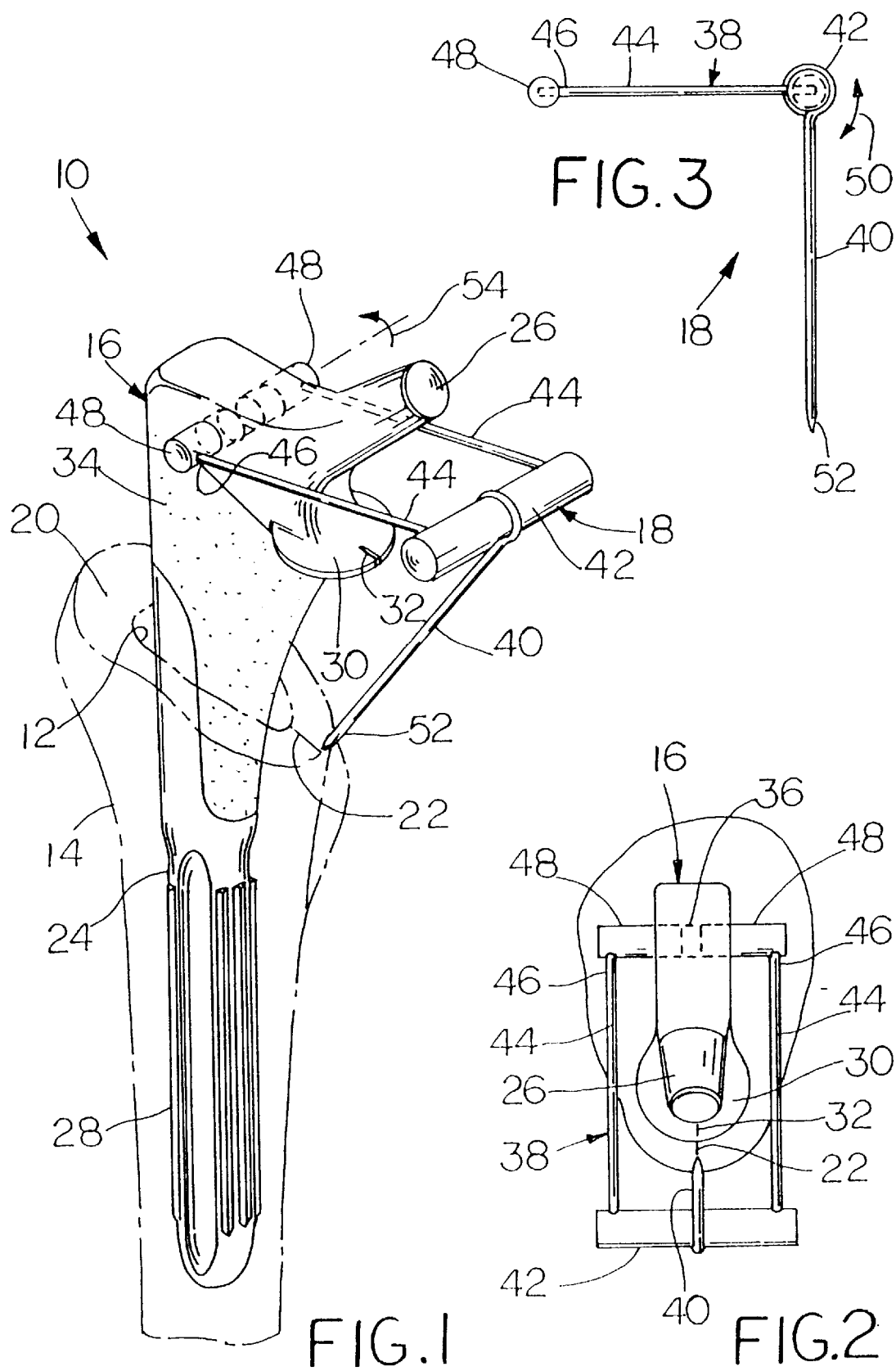

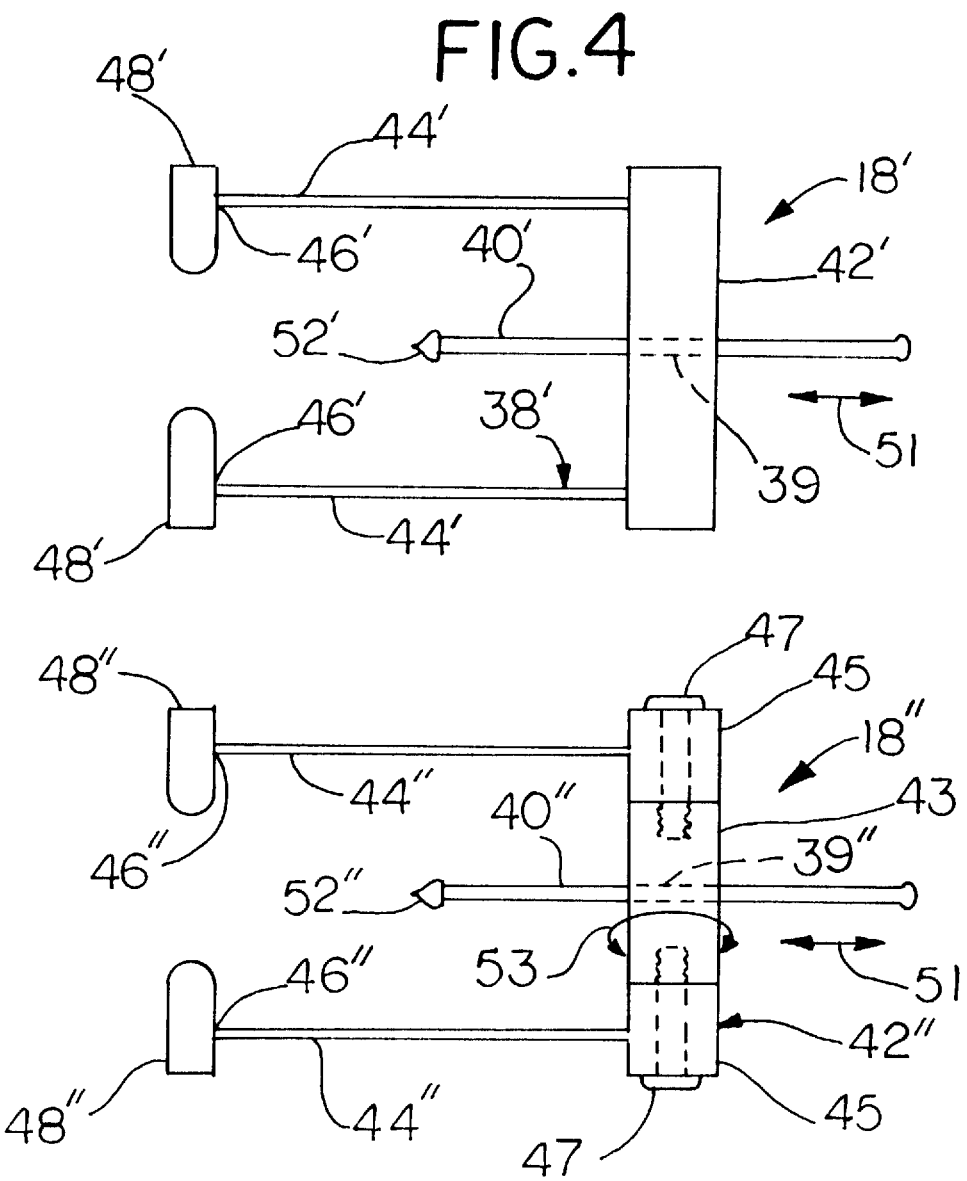

ROTATIONAL ALIGNMENT GUIDE FOR A PROSTHETIC HIP STEM IMPLANT AND METHOD OF USING SAME

BACKGROUND OF THE INVENTION

1. Field of the Invention.

The present invention relates to prosthetic hip stem implants, and, more particularly, to a device for aligning a prosthetic hip stem implant.

2. Description of the Related Art.

A prosthetic hip stem implant typically includes a neck and a stem. The neck is disposed at a predetermined angular orientation relative to the longitudinal axis of the stem, which may vary depending upon the particular make and model of hip stem implant which is utilized.

It is known to align a prosthetic hip stem implant relative to an opening in a proximal femur prior to fully seating the hip stem implant within the opening. One known hip stem implant includes a visual indicia on a lip extending therefrom. The surgeon aligns the visual indicia on the lip of the hip stem implant with a visual alignment mark which is created on the calcar surface of the proximal femur. The hip stem implant typically includes a plurality of longitudinally extending self cutting splines around the periphery thereof which engage the cortical bone in the opening of the proximal femur. With such a hip stem implant, it is necessary to align the visual indicia on the lip with the visual alignment mark on the calcar surface prior to engagement between the self cutting splines and cortical bone of the proximal femur. This alignment is necessary because the hip stem implant cannot be rotated in the proximal femur after the grooves are cut therein by the self cutting splines. Aligning the visual indicia on the lip of the hip stem implant with the visual alignment mark on the calcar surface of the proximal femur can at times be difficult.

What is needed in the art is an alignment device which relatively accurately aligns the hip stem implant relative to the opening formed in the proximal femur prior to engagement between the self cutting splines of the hip stem implant and the cortical bone of the proximal femur.

SUMMARY OF THE INVENTION

The present invention provides a rotational alignment guide which attaches to an extraction hole on a hip stem implant and is used to align the hip stem implant prior to seating of the implant in an opening in a proximal femur.

The invention comprises, in one form thereof, an alignment device for aligning a prosthetic hip stem implant with an opening formed in a proximal femur. The hip stem implant includes a landmark and the proximal femur includes a visual alignment mark. The alignment device includes an implant engaging portion configured for attachment with the landmark on the hip stem implant. The alignment device also includes a needle indicator connected with the implant engaging portion and having an end which may be positioned relative to the visual alignment mark on the proximal femur, thereby aligning the prosthetic hip stem implant relative to the opening in the proximal femur.

An advantage of the present invention is that the prosthetic hip stem implant may be effectively aligned prior to engaging the self cutting splines of the implant with the cortical bone of the proximal femur.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

FIG. 1 is a perspective view of an embodiment of an alignment guide of the present invention, shown in relation to a proximal femur;

FIG. 2 is a top view of the alignment guide shown in FIG. 1; and

FIG. 3 is a side view of the alignment guide shown in FIGS. 1 and 2.

FIG. 4 is a plan view of an alternative embodiment of the alignment guide.

FIG. 5 is a plan view of a second alternative embodiment of the alignment guide.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings, there is shown an embodiment of a femoral implant assembly 10 of the present invention for use in association with an opening 12 formed in a proximal femur 14. Femoral implant assembly 10 generally includes a prosthetic hip stem implant 16 and a rotational alignment guide 18.

Proximal femur 14 includes a proximal end 20 which is shaped using known techniques. Opening 12 extends from end 20 along the intramedullary canal of proximal femur 14. Opening 12 is likewise formed using known techniques such as rasping and reaming. Proximal femur 14 includes a visual reference which may be used to align hip stem implant 16 relative to opening 12. In the embodiment shown, proximal femur 14 includes a visual reference in the form of a visual alignment mark 22 created on the calcar surface (not numbered) of end 20 of proximal femur 14. Visual alignment mark 22 may be formed by a projection extending from a reamer (not shown) used to ream opening 12, or by manually placing a mark on the calcar surface of end 20. It is also to be understood that the visual reference may be other than a visual alignment mark 22 which is placed on proximal femur 14. For example, the visual reference may be a selected anatomical visual reference on proximal femur 14.

Prosthetic hip stem implant 16 includes a stem 24 and a tapered neck, in known manner. Stem 24 includes a plurality of self cutting splines 28 which inhibit relative rotational movement between hip stem implant 16 and proximal femur 14 when hip stem implant 16 is seated within opening 12. Neck 26 is configured for attachment with a femoral head (not shown), in a known manner. Hip stem implant 16 also includes a collar 30 with an alignment indicia 32 thereon. Alignment indicia 32 is intended to align with visual alignment mark 22 when hip stem implant 16 is seated within opening 12 of proximal femur 14. A porous metal surface 34 enhances attachment between hip stem implant 16 and proximal femur 14 by allowing bony ingrowth therein or attachment with bone cement, depending upon the particular application.

Hip stem implant 16 also includes a landmark allowing rotational alignment guide 18 to be attached therewith, as will be described hereinafter. In the particular embodiment shown, hip stem implant 16 includes a landmark in the form of an extraction hole 36 which is typically used to extract femoral implant 16 from proximal femur 14 during a revision surgery. It is to be understood, however, that the landmark on hip stem implant 16 allowing attachment with rotational alignment guide 18 may be any suitable structural portion of hip stem implant 16.

Rotational alignment guide 18 includes an implant engaging portion 38 and a needle indicator 40. Implant engaging portion 38, in the embodiment shown, is in the form of a U-shaped portion having a cross arm 42 which interconnects a pair of arms 44. Each arm 44 has an end 46 with a locator projection 48 attached therewith. Each locator projection 48 extends into extraction hole 36 and interconnects implant engaging portion 38 with hip stem implant 16. As will be appreciated, arms 44 may be flexed to allow locator projections 48 to be inserted into and removed from extraction hole 36 defining the landmark on hip stem implant 16. Locator projections 48 are shown as being separate from and attached with arms 44. However, it will be appreciated that locator projections 48 may also be integrally formed with arms 44. Similarly, cross arm 42 may also be integrally formed with arms 44.

Needle indicator 40 is pivotally connected with implant engaging portion 38, as indicated by arrow 50 in FIG. 3. More particularly, cross arm 42 includes an annular groove (not shown) which pivotally carries needle indicator 40. Needle indicator 40 includes an end 52 which may be positioned relative to visual alignment mark 22 on proximal femur 14, whereby hip stem implant 16 may be aligned relative to opening 12 prior to engaging self cutting splines 28 with the cortical bone in opening 12 of proximal femur 14.

In use, opening 12 is formed in proximal femur 14 using known techniques such as rasping and/or reaming. A visual reference is identified on proximal femur 14, such as a visual alignment mark 22 created on the calcar surface of proximal femur 14. Visual alignment mark 22 may be formed either manually or by a projection extending from the reamer used to form opening 12. Thereafter, stem 24 of hip stem implant 16 is inserted into opening 12. However, self cutting splines are not fully engaged with the cortical bone of proximal femur 14, so as to allow relative rotational movement between hip stem 16 and proximal femur 14. Rotational alignment guide 18 is attached to the physical landmark on hip stem implant 16 by inserting locator projections 48 into extraction hole 36, Rotational alignment guide 18 may thus pivot about the longitudinal axis of locator projections 48 as indicated by arrow 54 (FIG. 1). Hip stem implant 16 is then rotated about the longitudinal axis of stem 24 in a manner such that end 52 of needle indicator 40 is aligned with visual alignment mark 22 on proximal femur 14 (FIG. 1). Hip stem implant 16 is then moved into opening 12 such that self cutting splines 28 cut the cortical bone in opening 12 until collar 30 is fully seated against end 20 of proximal femur 14. Rotational alignment guide 18 simply rotates up and out of the way as hip stem implant 16 is seated within opening 12 of proximal femur 14. Alternatively, rotational alignment guide 18 may be removed from hip stem implant 16 after sufficient engagement between self cutting splines 28 and proximal femur 14. Rotational alignment guide 18 is removed from hip stem implant 16 by flexing arms 44 such that locator projections 48 disengage extraction hole 36.

An alternative embodiment of the alignment guide 18 of FIGS. 1–3 is illustrated in FIG. 4. Alignment guide 18' includes an implant engaging portion 38' and a needle indicator 40'. Implant engaging portion 38', in the embodiment shown, is in the form of a U-shaped portion having a cross arm 42' which interconnects a pair of arms 44'. Each arm 44' has an end 46' with a locator projection 48' attached therewith. Each locator projection 48' extends into an extraction hole of a hip stem implant and interconnects implant engaging portion 38' with a hip stem implant. As will be appreciated, arms 44' may be flexed to allow locator projections 48' to be inserted into and removed from the extraction hole defining the landmark on hip stem implant in a manner consistent with the preferred embodiment. Locator projections 48' are shown as being separate from and attached with arms 44'. However, it will be appreciated that locator projections 48' may also be integrally formed with arms 44'. Similarly, cross arm 42' may also be integrally formed with arms 44'.

Needle indicator 40' is shiftably carried by cross arm 42' as indicated by arrow 51 in FIG. 4. More particularly, cross arm 42' includes an through bore 39 which accommodates needle indicator 40'. Needle indicator 40' includes an end 52' which may be positioned relative to a visual alignment mark on proximal femur consistent with the preferred embodiment. However, instead of rotatably moving relative to cross bar 42, needle indicator 40' slides in the direction of arrow 51.

A third embodiment of the alignment guide 18 of FIGS. 1–3 is illustrated in FIG. 5. Alignment guide 18" includes an implant engaging portion 38" and a needle indicator 40". Implant engaging portion 38", in the embodiment shown, is in the form of a U-shaped portion having a cross arm 42" which interconnects a pair of arms 44". Cross arm 42" includes outer portions 45 connected to arms 44" and a center portion 43. Center portion 43 is connected to outer portions 45 by a pair of screws 47 such that the center portion 43 is rotatable relative to outer portions 45. Each arm 44" has an end 46" with a locator projection 48" attached therewith. Each locator projection 48" extends into an extraction hole of a hip stem implant and interconnects implant engaging portion 38" with a hip stem implant. As will be appreciated, arms 44" may be flexed to allow locator projections 48" to be inserted into and removed from the extraction hole defining the landmark on hip stem implant in a manner consistent with the preferred embodiment. Locator projections 48" are shown as being separate from and attached with arms 44". However, it will be appreciated that locator projections 48" may also be integrally formed with arms 44". Similarly, cross arm 42" may also be integrally formed with arms 44".

Needle indicator 40" is shiftably carried by cross arm 42" as indicated by arrow 51 in FIG. 4. More particularly, cross arm 42" includes an through bore 39" which accommodates needle indicator 40". Needle indicator 40" includes an end 52" which may be positioned relative to a visual alignment mark on proximal femur consistent with the preferred embodiment. However, instead of merely rotatably moving or merely sliding relative to cross bar 42, needle indicator 40" slides in the direction of arrow 51 and rotates with center portion 43 in the direction of arrow 53.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A femoral implant assembly for use in association with an opening formed in a proximal femur, the proximal femur including a visual reference, said femoral implant assembly comprising:

a prosthetic hip stem implant including a landmark; and an alignment guide including an implant engaging portion and a needle indicator, said implant engaging portion configured for attachment with said landmark on said hip stem implant, said needle indicator connected with said implant engaging portion and having an end which may be positioned relative to the visual reference on the proximal femur, whereby said prosthetic hip stem implant is aligned relative to the opening in the proximal femur, wherein said landmark on the hip stem comprises an extraction hole and wherein said implant engaging portion comprises a generally U-shaped portion having a pair of arms, each said arm having an end with a locator projection, each said locator projection extending into said extraction hole.

2. The femoral implant assembly of claim 1, wherein said U-shaped portion comprises a cross arm interconnecting said arms.

3. The femoral implant assembly of claim 1, wherein said hip stem implant includes a stem having a plurality of self cutting splines.

4. The femoral implant assembly of claim 1, wherein said needle indicator is pivotally connected with said implant engaging portion.

5. The femoral implant assembly of claim 1, wherein the visual reference on the proximal femur comprises a visual alignment mark on a calcar surface of the proximal femur.

6. An alignment device for aligning a prosthetic hip stem implant with an opening formed in a proximal femur, the hip stem implant including a landmark and the proximal femur including a visual alignment mark, said alignment device comprising:

an implant engaging portion configured for attachment with the landmark on the hip stem implant; and a needle indicator connected with said implant engaging portion, said needle indicator having an end which may be positioned relative to the visual alignment mark on the proximal femur, thereby aligning said prosthetic hip stem implant relative to the opening in the proximal femur, wherein said implant engaging portion comprises a generally U-shaped portion having a pair of arms, each said arm having an end with a locator projection, each said locator projection being configured for attachment with the landmark on the hip stem implant.

7. The alignment device of claim 6, wherein said U-shaped portion comprises a cross arm interconnecting said arms.

8. The alignment device of claim 6, wherein said needle indicator is pivotally connected with said implant engaging portion.

9. The alignment device of claim 6, wherein said alignment device comprises a rotational alignment guide.

* * * * *